United States Patent
Graham et al.

(10) Patent No.: US 7,241,845 B2
(45) Date of Patent: Jul. 10, 2007

(54) RANDOM BLOCK COPOLYMERS

(75) Inventors: Neil Bonnette Graham, Glasgow (GB); Christopher Raymond Moran, Glasgow (GB)

(73) Assignee: Ocutec Limited, Glasgow (GB)

( * ) Notice: Subject to any disclaimer, the term of this patent is extended or adjusted under 35 U.S.C. 154(b) by 245 days.

(21) Appl. No.: 10/805,494

(22) Filed: Mar. 22, 2004

(65) Prior Publication Data

US 2004/0198901 A1 Oct. 7, 2004

Related U.S. Application Data

(63) Continuation of application No. 09/020,670, filed on Feb. 9, 1998, now abandoned, which is a continuation of application No. 08/530,160, filed on Oct. 24, 1995, now abandoned.

(30) Foreign Application Priority Data

Apr. 1, 1993 (GB) .................. 9306887.2
Mar. 31, 1994 (GB) ............... PCT/GB94/00699

(51) Int. Cl.
*C08G 65/32* (2006.01)
(52) U.S. Cl. ........................ 525/403; 528/76
(58) Field of Classification Search ................ 525/403; 528/76
See application file for complete search history.

(56) References Cited

U.S. PATENT DOCUMENTS

| 3,607,837 A | 9/1971 | Reegen et al. |
| 3,627,714 A | 12/1971 | Merkyl |
| 4,849,458 A | 7/1989 | Reed et al. |
| 4,920,172 A | 4/1990 | Daoud |
| 5,000,955 A | 3/1991 | Gould et al. |
| 5,061,777 A | 10/1991 | Yoda et al. |
| 5,120,816 A | 6/1992 | Gould et al. |

FOREIGN PATENT DOCUMENTS

| EP | 0 299 758 | 1/1989 |
| EP | 0 481 600 A2 | 4/1992 |
| FR | 2 373 279 | 7/1978 |
| WO | 91/02763 | 3/1991 |

OTHER PUBLICATIONS

"CRC Handbook of Chemistry and Physics," 64th ed., Weast (ed.), CRC Press, Boca Raton, FL, p. C-218 (1983).
Yui et al, J. Controlled Release, vol. 6, pp. 329-342.
Yu, J. et al, "Blood interactions with novel polyurethaneurea hydrogels"; Biomaterials, vol. 12, No. 12;pp. 119-120 (Mar. 1991).

*Primary Examiner*—Bernard Lipman
(74) *Attorney, Agent, or Firm*—Nixon & Vanderhye

(57) ABSTRACT

A linear random block copolymer comprising segments of polyethylene oxide and a relatively more hydrophobic polymer, e.g. polypropylene oxide connected by hydrophobic segments containing urethane and urea groups formed from the reaction of a di-isocyanate and a diamine, wherein the diamine comprises less than 2% by weight of the total weight of the reactants used in the preparation of the copolymer.

21 Claims, 3 Drawing Sheets

RANDOM BLOCK COPOLYMERS

This application is a continuation of application Ser. No. 09/020,670, filed Feb. 9, 1998, now abandoned, which is a continuation of application Ser. No. 08/530,160, filed Oct. 24, 1995, now abandoned, the entire content of which is hereby incorporated by reference in this application.

This invention relates to linear random block copolymers, to processes for their production and their use.

Polymeric hydrogel compositions comprising chemically cross-linked polyalkylene glycols and their use in controlled release compositions have been described e.g. in British Patents 2047093 and 2047094. The cross-linking of these compositions was found to be essential for the production of water insoluble hydrogels since the omission of the cross-linking agent led to the production of urethane chain-extended polyalkylene glycols which were not water insoluble and which had insufficient mechanical strength. Whilst these compositions exhibit highly desirable release properties the cross-linked nature of these polymers means that their fabrication into useful devices can only be achieved by casting the reactant mixture. Although simple shapes can be produced relatively easily the fabrication of more complex shapes will normally require a machining step.

British Patent 1551620 describes linear block polymers which are useful as components of controlled release compositions wherein the polymers are amphipathic materials comprising alternating blocks of hydrophilic and hydrophobic regions. The polymers preferably comprise at least 30% by weight of hydrophilic regions. Not all the polymers disclosed therein are completely insoluble in water. Yui et al. in Journal of Controlled Release, 6, 1987, pp 329-342 describe multi-block copolymers consisting of sequences of soft and hard segments which form a microphase separated structure composed of hard segment clusters and surrounding soft segment matrices, the actual materials reported being segmented polyether-poly(urethane-urea)s having a urea content of from 4.5 to 6.1% by weight of final copolymer. The process used to produce the copolymers in Yui et al. comprises a three-step prepolymer solution polymerisation using an aromatic di-isocyanate to initially end-cap the monomers followed by the addition of an aliphatic diamine (3-4% by weight of total reactants), the end product copolymer being insoluble in methanol.

European Patent Application 205815 discloses the preparation of copolymers of polyethylene glycol and selected amines and di-isocyanates using three-step polymerisation reaction similar to that of Yui et al. supra. The resultant copolymers have a urea content of over 5% by weight of the final polymer and are only soluble in harsh solvents.

UK Patent 2,235,462B discloses solvent soluble linear chain extended polymers comprising hydrophilic predominantly polyalkylene oxide segments connected by a hydrophobic hydrogen bonding chain extending group. Such polymers are believed to be of a structure wherein the hydrogen bonding regions are closely associated, resulting in the polyalkylene oxide regions aligning themselves between successive hydrogen bonding regions.

For many uses it is particularly advantageous to have a polymer of high mechanical strength especially in the swollen state.

It has now been found that this objective can be achieved with linear random block copolymers comprising hydrophilic predominantly polyethylene oxide segments i.e. $-(CH_2CH_2O)_n-$, segments of relatively more hydrophobic character, and hydrophobic connecting segments containing urethane —NHCOO— groups and urea —NHCONH— groups connecting the hydrophilic and relatively more hydrophobic segments, in which the urea groups comprise from 0.1 to 5.0% by weight of the polymer.

The copolymers of this invention may be described as solvent soluble polymers, i.e. soluble rather than merely swellable in at least one organic solvent medium, preferably a polar organic solvent such as a chlorinated hydrocarbon solvent e.g. chloroform or an alcohol such as methanol.

In the linear random block copolymers of this invention the hydrophilic segments comprise predominantly polyethylene oxide (PEO) residues. These residues may comprise a minor amount of an additional component consistent with maintaining the desired hydrophilicity of these segments. Usually the proportion of such a component will comprise no more than 25% and preferably no more than 10% by weight of the hydrophilic segment. Examples of co-monomers from which the additional component is derived include other alkylene oxides, epihalohydrins, cyclic mono or poly ethers such as oxetane, tetrahydrofuran, dihydrofuran, dihydropyran, dioxolane and trioxane and N[epoxy substituted] heterocyclic compounds such as N-[2,3-epoxypropyl]-pyrolidone. For example the hydrophilic segment may comprise a polyethylene oxide and up to 25%, preferably up to 20%, by weight of propylene oxide, 1,2, epoxybutane or 2,3, epoxybutane.

Hydrophilic segments of the kind described above have been utilised in the linear chain-extended polymers described in our prior patent GB 2,235,462B (U.S. Pat. No. 5,236,966). In contrast, the copolymers of the present invention contain hydrophobic polymer segments additional to such hydrophilic segments and disposed randomly in the polymer chain as discrete blocks. In such random block copolymers it is preferred that the relatively more hydrophobic segments are derived from a polymer which is sufficiently compatible with the polyethylene oxide (PEO) to form a homogeneous melt or solvent solution of the component polymers from which the copolymer product can be formed by the polymerisation reactions described hereinafter. Thus the hydrophobic segments may comprise polypropylene oxide (PPO) segments i.e. $-(CH(CH_3)CH_2O-)_n-$ or segments of other repeating units which provide the desired degree of hydrophobicity. Some examples of alternative blocks which may be used in conjunction with polyethylene glycol to produce strong, linear PUU hydrogels are hydroxy-terminated polyols derived from polytetramethylene oxide, polyisobutylene, polyethylene adipate, polytetramethylene adipate, polycaprolactone, polybutadiene and hydroxybutyl terminated polydimethylsiloxane.

In the copolymers of the present invention the hydrophilic and hydrophobic segments are connected in a random manner to adjoining segments by urethane and urea linkages. Through either of such linkages the connections are from hydrophilic to hydrophilic, hydrophilic to hydrophobic and hydrophobic to hydrophobic segments. The urethane linkages predominate over the urea linkages.

The relative proportions of the hydrophilic PEO segments and the relatively more hydrophobic segments, e.g. PPO segments, may be varied widely in accordance with the properties desired in the resultant copolymer. Very attractive wet strength properties have been found with copolymers respectively containing from 5 to 90% PEO and 55 to 5% PPO, especially from 30 to 60% PEO and from 45 to 15% PPO.

In accordance with a particularly preferred aspect of this invention the polyethylene oxide segments may have a number average molecular weight from 1,000 to 12,000 or even higher, (for example 20,000) suitably from 2,000 to 8,000. The polypropylene oxide segments may have a number average molecular weight of from 250 to 6,000. Those segments which exhibit crystallinity are preferred insofar as the property may permit convenient purification techniques to be practised and lead to higher strength copolymers in the dry state.

The copolymers of the present invention are of particular advantage in that they retain their strength in the swollen "wet" state as distinct from the prior art polymers and copolymers which lose a significant proportion of their dry strength when they are swollen in water or other solvents.

The copolymers of the present invention may be characterised in that the normalised energy to break the copolymers in the swollen state is greater than that of the solvent soluble chain extended polymers derived from polyethylene oxide. e.g. in accordance with GB 2,235,462B. The normalised energy to break is described hereinafter.

Thus, the copolymers of the present invention may be further characterised in that the energy to break the copolymers in the dry state, as calculated by measuring the area under the curve of the stress-strain isotherm, is retained when the copolymers are swollen. Preferably the energy to break of the swollen copolymer is at least 15% of that of the copolymer in the dry state.

The urethane linkages in the copolymers of the present invention may be produced by reaction of hydroxy-terminated PEO-type hydrophilic polymers and hydroxy-terminated PPO-type or other type of more hydrophobic polymers with di-isocyanates. To provide the desired minor proportion of urea linkages it is necessary to introduce amine groups into the reaction. This may be achieved by adding to the reaction mixture from 0.2 to 2% of a diamine which will combine with some of the isocyanate groups to form the —NHCONH— linkage. Alternatively, a proportion of the hydrophilic and/or hydrophobic polymers utilised for the reaction may be amine-terminated. A further alternative is to utilise amineol-terminated polymers, i.e. OH-terminated at one end and NH$_2$-terminated at the other end. Thus the invention comprises a process for preparing a linear random block copolymer which comprises reacting a hydrophilic polymer consisting predominantly of polyethylene oxide with a relatively more hydrophobic polymer and a di-isocyanate, the amount of di-isocyanate being in excess of the stoichiometric amount required to produce the urethane and urea linkages, said reaction being conducted in the presence of reactive amino groups, the amino groups being provided by an added diamine reagent, when the reacting polymers are both hydroxy-terminated, or by one or more of the reacting polymers themselves when these are terminated by at least one amino group, the amount of reactive amino groups being no greater than that corresponding to 2% by weight of the added diamine, based on the total weight of reactants used.

Thus, a polyalkylene glycol may be reacted with a di-isocyanate in the presence of a diamine. Reaction of the glycollic hydroxyl groups with the isocyanate groups results in a proportion of connecting segments comprising urethane groups while reaction of the amine groups with the isocyanate groups results in a proportion of connecting segments comprising urea groups. The reaction may be carried out in the presence of a quantity of a di-isocyanate R(NCO)$_2$ at least sufficient to satisfy the stoichiometric requirement of one functional group per active hydrogen atom in the hydrophilic reactants. The resultant polymers comprise hydrophobic connecting segments which contain urethane and urea groups for example having the formula I

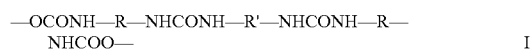

—OCONH—R—NHCONH—R'—NHCONH—R—NHCOO—   I wherein R represents a hydrocarbyl residue derived from the di-isocyanate, e.g. comprising from 2 to 20 carbon atoms, and R' represents a hydrocarbyl residue derived from the diamine, e.g. comprising from 2 to 20 carbon atoms.

In an alternative method of producing polymers in accordance with this invention a controlled minor proportion of the polyalkylene glycol is converted to a derivative having terminal amine groups. Such a conversion may be effected using known methods. The amine groups react with a di-isocyanate to produce a hydrophobic connecting segment, for example one having the formula II

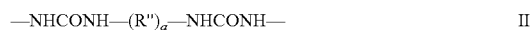

—NHCONH—(R")$_a$—NHCONH—   II wherein a is 0 or 1 and R" derives from the di-isocyanate and may represent a hydrocarbyl group having from 2 to 20 carbon atoms or a group derived from a prepolymer formed by the reaction of two molar proportions of a di-isocyanate with one molar proportion of a polyalkylene glycol or an amine capped derivative thereof, or a group having the formula —[R'''—X—R''']$_n$ wherein R''' represents a hydrocarbyl group having from 2 to 20 carbon atoms, X represents a polyalkylene oxide chain and n is an integer having a value of at least 1.

The isocyanate which may be employed in these reactions may be an aromatic, aliphatic or cycloaliphatic di-isocyanate or a bis-isocyanate terminated prepolymer. The use of aliphatic or cycloaliphatic di-isocyanates comprising from 2 to 20 carbon atoms per molecule is preferred. Examples of useful di-isocyanates include 1,6 hexamethylene di-isocyanate, isophorone di-isocyanate, 4,4' dicyclohexyl methane di-isocyanate, cyclohexylene 1,2 and 1,4 di-isocyanates, 4,4 diphenyl methane di-isocyanate, toluene 2,4 di-isocyanate and toluene 2,6 di-isocyanate.

The reaction with the polyethylene glycol or propylene glycol may utilise any aromatic, aliphatic or cycloaliphatic diamine which is compatible with the polymerisation system. Aliphatic diamines are highly preferred for many purposes. Any of the diamines which can be produced by the hydrolysis of any of the di-isocyanates referred to above may be utilised. Preferably the diamine comprises two primary amine functions and does not comprise any secondary amine functions. The presence of tertiary amino groups may be desirable in some instances. Examples of preferred diamines include hydrazine, bis-4-amino cyclohexyl methane, 1,6hexamethylene diamine and especially 4,4-diamino diphenyl methane.

A preferred form of di-isocyanate prepolymer which may be reacted with the amino derivative of the polyethylene glycol or propylene glycol are prepolymers formed by the reaction of two molar proportions of a di-isocyanate with one molar proportion of a polyethylene glycol or polypropylene glycol, or to an amine capped derivative thereof. Any of the di-isocyanates hereinbefore described may be utilised to produce such a prepolymer. The nature of the residue R" in formula II will correspond to the composition of that prepolymer.

In all these syntheses the proportion of urea linkages in the final polymer may be controlled by control of the proportion of amine groups introduced as reactants. Where the amine is to be generated in situ by hydrolysis of a di-isocyanate the quantity of water employed should be carefully controlled so as to avoid the formation of polymers having a significant degree of insolubility in organic solvents.

The random block copolymers of the present invention comprising urethane and urea linkages between the random blocks are referred to hereinafter as polyurethaneurea copolymers (PUU copolymers).

In accordance with a further preferred feature of this invention, it is found that copolymers of the invention with advantageous mechanical properties, for example enhanced toughness, are formed when the di-isocyanate is present in stoichiometric excess, preferably a small stoichiometric excess such as from 1% to 10%, preferably from 1% to 5%, by weight of the di-isocyanate above the stoichiometric requirement of one functional group per active hydrogen atom of the total reactants. Higher stoichiometric excess may result in the undesirable formation of insoluble copolymer. Thus, the excess of di-isocyanate must not be so great as to result in cross-linkage of the polymers.

The copolymers of the present invention may be prepared by forming a homogeneous melt or a solution of the polyethylene oxide and the more hydrophobic polymer, e.g. polypropylene oxide and then adding the necessary agent or reagents optionally with heating and the addition of catalyst. The reaction may be most conveniently performed in the absence of solvents but solvents may be desirable when using high molecular weight starting materials such as polyethylene glycols having number average molecular weights of greater than say 8000 or where the object is to produce a solution of the copolymeric material in a solvent. The reaction rate is reduced in the presence of solvent which undesirably prolongs the polymerisation process. In the case of di-isocyanate chain extending agents Lewis acid species such as ferric chloride are useful catalysts particularly when the products are intended for medical or pharmaceutical applications although other conventional catalysts known to be effective in urethane group formation such as stannous octoate, dibutyl tin dilaurate or tertiary amines may be employed.

It is desirable that the hydrogels are swellable often above 2×, for example from 3× to 10× or more, by weight in aqueous media. It is also preferred that the glass transition temperature is below the service temperature (that is, the expected temperature of the copolymer in use) and, preferably, below ambient temperature, that is the polymer is elastomeric.

The copolymers of the invention may be formed as blocks, foam, sheet, film, fiber or powder, and as such they are especially suited for use in bio-medical applications by formation of films, tubes, stents and catheters. The improved mechanical strength of the copolymers when in the swollen state also makes them especially useful in the coating of tablets whereas prior art polymeric coatings have tended to disintegrate upon exposure to a liquid environment.

The polyurethaneurea (PUU) copolymers of the present invention have the further advantage that when complexed with a polyacid, e.g. polyacrylic acid (PAA) or polymethacrylic acid, they can be used to form novel complex membranes which are insoluble across a wide pH range. These can be readily cast from appropriate solvents to form stable membranes which, by varying the ratio of the two components of the complex, provide a wide variety of acid complexed films with different responses to pH change. The PUU/PAA complexed membranes show a marked change in their degree of swelling over a narrow range of pH and are a promising class of "responsive" membranes. The change in swelling at particular (but varied) "critical" pH values can be utilised for the control of diffusate flux with pH and the presence of ionisable acid groups within the membrane structures gives the potential for a highly selective family of membranes for the separation of charged from neutral species.

This invention also provides a controlled release composition which comprises a copolymer as herein defined having incorporated therein an active substance, particularly a biologically active substance, for example a medication system. By "medication system" is meant any physiologically active substance or substances desired for use in vivo, either for prophylaxis or therapy.

The present invention is of broad applicability in the formulation of active substances, particularly, but not exclusively, biologically active substances releasable at a controlled rate. Examples of classes of biologically active substances which may be incorporated in the controlled release compositions of the present invention include flavourings, pharmaceuticals, bacteriostats, viruscides, pesticides such as insecticides, nematicides, molluscicides and larvicides, herbicides, fungicides, algaecides, topical or dermatological agents, antifoulants for marine growth prevention, proteins, for example enzymes, peptides, microbiological and plant hydroculture salts and nutrients and preservatives, veterinary trace metal formulations, and other growth promoting factors used in animal husbandry; for example, anti-anaemia preparation and anabolic steroids. Of particular interest are compositions of the present invention comprising, as biologically active substance, at least one pharmaceutical.

The controlled release compositions of this invention are especially suited for bio-medical applications by formation into films, tubes, stents and catheters having excellent mechanical strength in the swollen state. Such compositions can usefully incorporate biocides to render the surfaces difficult to colonise by cells which may cause occlusion. By contrast they are bio and haemo compatible and may in many situations be used without such additives.

The compositions of this invention thus find wide application in medical and surgical, including veterinary, contexts and in horticulture and agriculture as well as outside these areas.

The active substance may possess some degree of water solubility although this may be relatively small. The active substances may be incorporated into the copolymer after this has been formed into an appropriate shape, in which case the active substance will be soluble in the solvent used to swell the polymeric hydrogel. Alternatively, the active substance may be dissolved or dispersed in either the polyethylene glycol or polypropylene glycol prior to the addition of the remaining reactants in any of the processes described above.

It is an advantage of the present invention that the polymeric hydrogel may be dissolved in an organic solvent, usually a polar organic solvent such as chloroform, ethanol/chloroform, methanol, ethanol, n-propanol, isopropanol, butan-2-one, nitrobenzene, methyl benzoate, butyrolactone, tetrahydrofuran or benzyl alcohol in which the active substance is also soluble or dispersible; and the solution or dispersion containing the active substance can then be solvent cast. This also allows the copolymers to be used as coatings on granules or on tablets providing excellent release profiles or used as film or pouches thus providing essentially constant release devices. Alternatively the active material may be incorporated into a hollow envelope of the hydrogel which can be sealed by the application of solvent or heat to the adjoining edges. The novel devices may also be formed by dry mixing the active material with the hydrogel copolymers and forming a device by compression moulding, injection moulding or extrusion processes.

Using dispersions or drug solutions in the solution of copolymer the mixed system can be applied as a film or coating. Thus such a system can be applied as topical coatings on humans, animals or inert surfaces. Direct application of liquid by brushing, wiping or aerosol is also possible.

Specific classes of medication system which may be used in a controlled release composition of the invention include abortifacients such as prostaglandins, hypnotics, sedatives, tranquilisers, anti-pyretics, anti-inflammatory agents, antihistamines, antitussives, anticonvulsants, muscle relaxants, anti-tumour agents, for example those for the treatment of malignant neoplasia, local anaesthetics, anti-Parkinson agents. topical or dermatological agents, diuretics, for example those containing potassium, such as potassium iodide, preparations for the treatment of mental illness, for example preparations containing lithium for use in the treatment of manic depression or containing prostaglandins for the treatment of schizophrenia, anti-spasmodics, antiulcer agents, preparations containing various substances for the treatment of infection by pathogens including anti-fungal agents, for example metronidazole, anti-parasitic agents and other anti-microbials, anti-malarials, cardiovascular agents, preparations containing hormones, for example androgenic; estrogenic and progestational hormones, notably steroids such as oestradiol, sympathomimetic agents, hypoglycaemic agents, contraceptives, nutritional agents, preparations containing enzymes of various types of activity for example chymotrypsin, preparations containing analgesics, for example aspirin, and agents with many other types of action including nematocides and other agents of veterinary application. Mixtures of active substances may be incorporated into the controlled release compositions.

The controlled release compositions of this invention may be used as a contraceptive composition suitably containing, as active subtances, at least one natural or synthetic steroid sex hormone for example an oestrogen or progestogen. Suitable progestogens include the natural progesterone and its synthetic analogues, including 11-dehydro-progesterone, delalutin, 21-fluoro-17-acetoxy-6-methylprogesterone, medroxyprogesterone acetate, megestrol acetate, chlormadinone acetate, ethisterone, dimethisterone, A-norprogesterone, 19-norprogesterone, 21-norprogesterone, normethandone, norethynodrel, norethindrone and its acetate, D1- and D-norgestrel, norgestrienone, ethynodiol diacetate, lynstrenol, ethynylestradiol, retroprogesterone, dydrogesterone, norvinodrel, quingestranol acetate, norethisterone and its acetate and oenanthate, anagesterone acetate, medrogestone, clomagestone, allyl estrenol and cingestol, preferably progesterone. Suitably oestrogens include the natural β-oestradiol and its synthetic analogues, principally ethinyloestradiol or mestranol, preferably β-oestradiol.

The controlled release compositions of this invention are also useful in the treatment of diabetes and pernicious anaemia where, for example, the controlled release of insulin and cobalamin, respectively, may be utilised.

Moreover, the controlled release compositions of this invention are particularly suited to treatment, both prophylactic and therapeutic, of tropical diseases; for example, malaria, leprosy, schistosomiasis and clonorchiasis. Examples of drugs which can be used as biologically active substances in sustained release compositions of this invention for the treatment of these and other tropical diseases include quinine, sulphanamides, rifamcin, clofazimine, thiambutosine, chlor-phenyl derivatives, chlorguamide, cycloguanil, pyrimethamine, sulpha-diazine, trimethoprim, quinoline derivatives such as pamaquine, chloroquine, pentaquine, primaquine and amodiquine, pararosaniline, sulphamethizole, quinacrine, dapsone, sodium sulphoxone, sulphetrone, sodium hydnocarpate and sodium chaulmoograte. Drugs of particular effectiveness are cycloguanil, pyrimethamine and sulphadiazine.

The controlled release compositions of this invention are also very well suited to veterinary applications. Examples include preparations of antibiotics for general antibacterial activity and also in the treatment of anaplasmosis in cattle; preparations for provision of a wide spectrum of activity against both ectoparasites, for example termites and endoparasites including arthropods, arrested larvae stages or nematodes, lungworms and general strongyles: these may comprise avermectins; preparations for provision of activity against tremotode, cestode and roundworm infections: these may comprise amoscanate and praziquantel; preparations for provision of activity against theileria in cattle: these may comprise biologically active naphthoquinones such as menoctone; preparations for provision of activity against babesiosis in cattle, horses and dogs: these may comprise berenil, amidocarb and diampron; preparations for provision of activity against liver fluke in sheep and cattle and against Haemonchus species: these may comprise closantel.

BRIEF DESCRIPTION OF THE DRAWINGS

The invention will now be described with reference to the accompanying drawings, in which.

Figure 1:
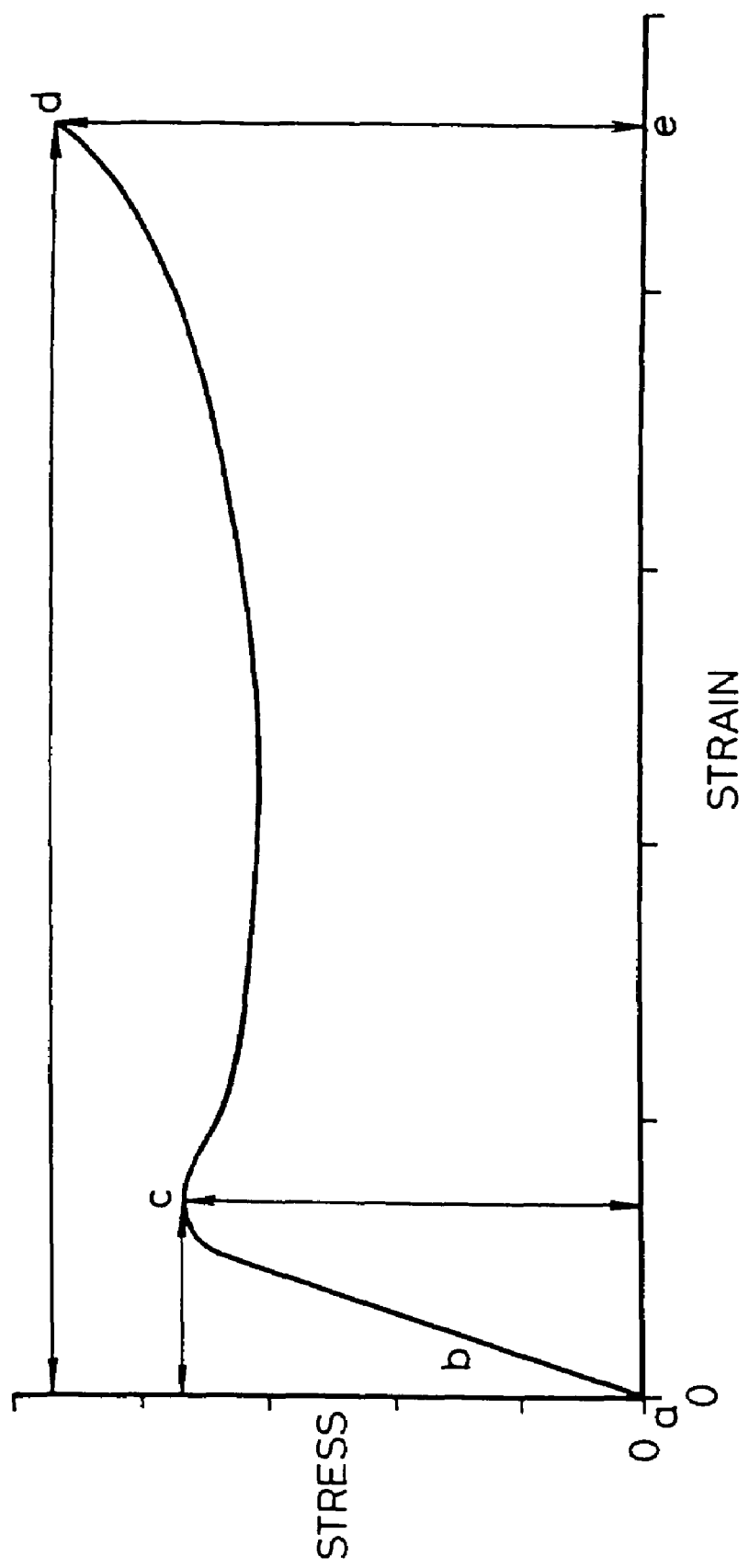
FIG. 1 is a generalized stress-strain isotherm.

The invention is illustrated by the following Examples.

EXAMPLES

Example 1

The Synthesis of the Linear Block Copolymer Polyurethaneurea Hydrogels

Materials

The materials used for the synthesis of the linear block copolymer polyurethaneurea hydrogels were as follows.

Polyethylene Glycol (PEG)

The PEG was manufactured by B.P. Chemicals and supplied by Honeywell and Stein Limited. The manufacturer designates each batch a number average molecular weight, e.g. PEG6000. This indicates that the average number molecular weight (Mn) falls within a range of 5000-7000. The Certificate of Analysis provided by the supplier specified a number average molecular weight of 5810, i.e. PEG5810. The Mn was determined accurately by hydroxyl end-group analysis (see 'Experiments in Polymer Science", E. A. Collins, J. Bares, F. W. Billmeyer, Wiley-Interscience, 362-367, 1973).

Polypropylene Glycol (PPG)

The polypropylene glycol was supplied by the Aldrich Chemical Company Limited. The Mn quoted was 425, i.e. PPG425. The PPG425 was used without further purification.

Dicyclohexylmethane 4,4'-di-isocyanate (hereinafter referred to as Desmodur W): Desmodur is a Registered Trade Mark.

The Desmodur W was supplied by Bayer and has a molecular weight of 262.5. The density of the Desmodur W was found to be 1.07. The Desmodur W was used without further purification.

4,4'-Diaminodiphenylmethane (DADP)

The 4,4'-Diaminodiphenylmethane was supplied by BDH Chemicals Limited. DADP has a molecular weight of 198.27 and was not further purified before use.

Anhydrous Ferric Chloride ($FeCl_3$)

The ferric chloride was supplied by the Aldrich Chemical Company and was used without further purification.

The Procedure for the Synthesis of the Linear Block Copolymer Polyurethaneurea, PUU, Hydrogels The successful synthesis of the range of linear block copolymer polyurethaneurea hydrogels was achieved through the careful optimisation and development of a series of polymer formulations. All of the reactions were "one shot" melt polymerisations.

Purification of Materials

Water reacts readily with isocyanates and therefore its presence in the reaction will affect the reaction stoichiometry and the nature of the final product. The PEG6000 and PPG425 polyols readily absorb moisture from the atmosphere and require thorough drying before use. The water is removed by drying each polyol under vacuum on a rotary-evaporator at 90-100° C. for a minimum of three hours. The dry PEG6000 and PPG425 are stored under vacuum until required.

The PUU hydrogels are prepared in the laboratory in 60 g batches which ensures that the reaction melt can be adequately stirred by hand after the addition of the Desmodur W and then poured, quickly, into suitable moulds (e.g. polypropylene test tubes or bottles).

The following procedure describes the preparation of PUU VII based on polyethylene glycol with a number average molecular weight of 5830, i.e. PEG5830. The same method is used in the preparation of all the copolymers, varying the amount of reactants according to Table 1 below. Appropriate quantities of the PEG5830 and PPG425 were weighed into round-bottom flasks. The flask containing the PEG5830 was placed in an oven at 95° C. until all of the PEG had melted. The PEG and PPG were each dried under vacuum on a rotary-evaporator for a minimum of 3 hours at 90-100° C. On completion of drying, the PEG5830 was stoppered, put under vacuum, and returned to the oven at 95° C. The flask containing the PPG425 was stoppered and allowed to cool to room temperature. 28.19 g of the dry PPG425 was weighted into a dry beaker. 0.2 mg/g total reactants of anhydrous ferric chloride was added and stirred in immediately to reduce moisture absorption from the atmosphere. The beaker was then placed in the oven at 95° C. until the catalyst had completely dissolved in the PPG425. 0.726 g of the diamine was then weighed accurately and added to the hot PPG/$FeCl_3$ solution and the beaker returned to the oven. Once the diamine had dissolved (15-30 minutes), 29.004 g of the molten, dry PEG5830 was added to the beaker and the mixture stirred vigorously before being returned to the oven for about 30 minutes, with occasional stirring. When the reactant mixture was up to temperature and homogeneous in appearance, 12.67 ml of Desmodur W was added from a burette inside a fumecupbaord. The addition was carried out quickly and with extreme caution due to the high toxicity of the di-isocyanate. The reaction mixture was then stirred vigorously for 1½-2 minutes before being poured carefully into preheated, polypropylene test tube moulds. The moulds were then placed in the oven at 95° C. for a reaction time of 20 hours.

The length of time for the polymerisations was based on the time taken for all the di-isocyanate to be reacted. The isocyanate group has a characteristic infra-red signal at approximately 2270 $cm^{-1}$. By monitoring the disappearance of this peak, the time taken for the reaction to go to completion could be determined. The length of time taken for the isocyanate peak to disappear varied between 15 and 20 hours for the different formulations. Hence, to ensure that all the polymerisations went to completion, the reaction time was set at 20 hours.

The PUU compositions were removed from the polypropylene moulds, swollen and washed to remove water-soluble material. The swollen blocks of hydrogel were chopped into small pieces, washed twice in fresh distilled water and then dried in air. The air-dried polymer pieces were then placed in a vacuum oven at room temperature until completely dry. The dry hydrogel pieces were sealed in sample bags and stored until required. Extractable material was, typically, less than 0.1% by weight of the hydrogel.

The PUU hydrogels are soluble in certain, relatively mild, organic solvents including chloroform, dichloromethane, methanol, ethanol propan-2-ol and methyl ethyl ketone. A variety of films, coatings, shapes and devices can be prepared using solvent-casting techniques.

Linear Polyurethaneureas Copolymers PUUs with a Constant Weight Content of Diamine The results of previous series of polymerisations indicated that the solubility of the PUUs in solvent was dependent on the amount of urea linkages in the polymer chains. A series of linear polyurethaneurea copolymers was prepared in which the diamine content, and consequently the urea content, was kept constant as a weight fraction of the final polymer. This new series of PUU copolymers was based on the compositions having a diamine weigh, content of 1.21% and a 5% excess of di-isocyanate over the stoichiometric requirement.

Example of Calculation to Obtain Weight Proportions of Reactants

|  | PEG5830 | PPG425 | DADP | Desmodur W (DW) |
|---|---|---|---|---|
| No. of moles | 1.0 | 8.0 | 0.736 | 10.223 |
| Dalton units | 5830 | 8.0 × 425 = 3400 | 0.736 × 198.27 = 145.926 | 10.223 × 262.5 = 2683.538 |
| Weight percent of reactants | 48.34 | 28.19 | 1.21 | 22.26 |
| Weight required in grams | 29.004 | 16.914 | 0.726 | 13.560 = 12.67 ml |

Catalyst concentration = 0.2 mg $FeCl_3$/g polymer

The compositions of the novel series of polyurethaneurea block copolymers are detailed in Tables 1 and 2. In both Tables, PUU I and PUU XIII are not linear block copolymers, but are linear chain extended polyalkylene oxide polymers as described in GB 2235462.

Table 1 shows the composition of the series of linear block copolymer polyurethaneureas (in molar ratios of components) prepared having a constant weight percentage of DADP (1.21% of total reactants) and a 5% excess of Desmodur W over stoichiometric requirement.

TABLE 1

| Polymer Reference | Wt. Percent | | Number of moles of | | |
| --- | --- | --- | --- | --- | --- |
| | PEG5830 | PEG5830 | PPG425 | DADP | DW |
| PUU I | — | — | 1.0 | 0.044 | 1.096 |
| PUU II | 10.01 | 1.0 | 72.0 | 3.554 | 80.382 |
| PUU III | 19.85 | 1.0 | 32.0 | 1.790 | 36.530 |
| PUU IV | 27.19 | 1.0 | 21.0 | 1.310 | 24.476 |
| PUU V | 35.60 | 1.0 | 14.0 | 1.000 | 16.800 |
| PUU VI | 43.18 | 1.0 | 10.0 | 0.824 | 12.415 |
| PUU VII | 48.34 | 1.0 | 8.0 | 0.736 | 10.223 |
| PUU VIII | 54.92 | 1.0 | 6.0 | 0.648 | 8.030 |
| PUU IX | 63.55 | 1.0 | 4.0 | 0.560 | 5.838 |
| PUU X | 68.98 | 1.0 | 3.0 | 0.516 | 4.742 |
| PUU XI | 75.41 | 1.0 | 2.0 | 0.472 | 3.646 |
| PUU XII | 83.18 | 1.0 | 1.0 | 0.428 | 2.549 |
| PUU XIII | 92.72 | 1.0 | — | 0.384 | 1.453 |

Table 2 shows the percent composition of the linear block copolymer polyurethaneureas prepared.

TABLE 2

| Polymer Reference | Weight Percentage of Total Polymer | | | |
| --- | --- | --- | --- | --- |
| | PEG5830 | PPG425 | DADP | DW |
| PUU I | — | 58.91 | 1.21 | 39.88 |
| PUU II | 10.01 | 52.54 | 1.21 | 36.24 |
| PUU III | 19.85 | 46.30 | 1.21 | 32.64 |
| PUU IV | 27.19 | 41.63 | 1.21 | 29.97 |
| PUU V | 35.60 | 36.31 | 1.21 | 26.88 |
| PUU VI | 43.18 | 31.48 | 1.21 | 24.13 |
| PUU VII | 48.34 | 28.19 | 1.21 | 22.26 |
| PUU VIII | 54.92 | 24.02 | 1.21 | 19.85 |
| PUU IX | 63.55 | 18.53 | 1.21 | 16.71 |
| PUU X | 68.98 | 15.08 | 1.21 | 14.73 |
| PUU XI | 75.41 | 11.00 | 1.21 | 12.38 |
| PUU XII | 83.18 | 6.06 | 1.21 | 9.55 |
| PUU XIII | 92.72 | — | 1.21 | 6.07 |

Example 2

The Preparation of PUU Hydrogel Films

The PUUs I to XIII prepared in Example 1 above were removed from the polypropylene bottles and the polymer blocks placed in beakers of double distilled water in order to extract any water soluble material. The PUUs were left to swell in the water over a period of 3-5 days. The swollen polymers were then cut into small pieces, dried on trays in air for 3 days and then in a vacuum oven for 48 hours. The water extractable material was found to be negligible, being less than 0.1% by weight of the original polymers, and was ignored in any subsequent calculations.

Films or sheets of the PUU material were prepared by solvent-casting on glass plates from 5% w/v solutions of the water-extracted PUUs in chloroform. The glass plates were scratch-free and bordered with SILASTIC silicone rubber sealant. The plate dimensions were approximately 30 cm×20 cm, with a SILASTIC border height of ~5 mm above the glass surface.

The plates were placed on a level work bench and the copolymer solutions poured onto the glass surface. A period of 24 hours was allowed for the complete evaporation of the chloroform. The films were removed from the plates by swelling them away from the glass surface using double distilled water. The films were then dried by carefully laying them out in air for 24 hours followed by 24 hours in a vacuum oven.

Example 3

A: The Swelling in Water of the Linear Block Copolymer Polyurethaneurea Films

The Equilibrium Swelling of the PUU Films in Water at 21° C.

Samples of the PUU hydrogels were cut from the solvent-cast films and weighed accurately. The samples were then immersed in double distilled water and left to equilibrate at room temperature (21° C.). The samples were removed from the water at timed intervals, blotted with lint-free tissue paper and weighed. The films were deemed to be fully swollen when they showed no further increase in weight. The time taken for the equilibrium swelling in water at 21° C. to be reached was approximately 48 hours for each PUU composition.

The swelling measurements for each PUU composition were carried out in triplicate and the resulting Equilibrium Water Uptake (E.W.U.) values were calculated from the average of the three measurements and quoted to the nearest whole number. The results of the Equilibrium Swelling Values for the series of linear block copolymer polyurethaneureas, PUUs, at 21° C. or are given in Table 3 below.

The Equilibrium Swelling Value or Equilibrium Water Uptake (E.W.U.), of the samples was calculated relative to the original sample weight and is quoted as parts per hundred (pph) of the dry polymer:

$$E.W.U. \text{ (pph)} = \frac{W(s) = W(d)}{W(d)} \times 100$$

where W(s)=Equilibrium Swollen Weight of Sample, g
W(d)=Initial Dry Weight of Sample, g The swelling measurements for each PUU composition were carried out in triplicate and the resulting E.W.U. values were calculated from the average of the three measurements and quoted to the nearest whole number.

The Equilibrium Water Content (E.W.C.), of the PUU samples was calculated using the equation:

$$E.W.U. \text{ (\%)} = \frac{E.W.U.}{E.W.U. + 100.0} \times 100$$

The Equilibrium PEO/Water Content of the PUU samples was calculated using the equation:

$$Eqm. \text{ PEO/Water Content (\%)} = \frac{E.W.U. + W(PEO)}{E.W.U. + 100.0} \times 100$$

where W(PEO)=PEO05830 Content of the Dry PUU, pph

TABLE 3

| Polymer Reference | Weight Percent PEO5830 | Equilibrium Water Uptake(pph) | Equilibrium Water Content(%) | Equilibrium PEG/Water |
| --- | --- | --- | --- | --- |
| PUU I | — | 4.0 | 3.85 | 3.85 |
| PUU II | 10.01 | 21.0 | 17.36 | 25.63 |
| PUU III | 19.85 | 58.0 | 36.71 | 49.27 |
| PUU IV | 27.19 | 82.0 | 45.05 | 59.99 |
| PUU V | 35.60 | 128.0 | 56.14 | 71.75 |
| PUU VI | 43.18 | 165.0 | 62.26 | 78.56 |

TABLE 3-continued

| Polymer Reference | Weight Percent Content(%) | Equilibrium Water Uptake(pph) | Equilibrium Water Content(%) | Equilibrium PEG/Water |
|---|---|---|---|---|
| PUU VII | 48.34 | 183.0 | 64.66 | 81.74 |
| PUU VIII | 54.92 | 218.0 | 68.55 | 85.82 |
| PUU IX | 63.55 | 298.0 | 74.87 | 90.84 |
| PUU X | 68.98 | 388.0 | 79.51 | 93.64 |
| PUU XI | 75.41 | 578.0 | 85.25 | 96.37 |
| PUU XII | 83.18 | 871.0 | 89.70 | 98.27 |
| PUU XIII | 92.72 | 2800.0 | 96.55 | 99.75 |

B: The Equilibrium Swelling of the PUU Films in Water at 37° C.

The Equilibrium Swelling Values for the series of linear block copolymer polyurethaneureas in water at 37° C. were calculated using the same method as described in Section A. The experiments were carried out in a Grant, Model SS40, Water Bath at 37° C.±0.1° C.

The results of the equilibrium swelling experiments, for the series of linear block copolymer polyurethaneureas in water at 37° C., are summarised in Table 4 below.

TABLE 4

| Polymer Reference | Weight Percent PEO5830 | Equilibrium Water Uptake(pph) | Equilibrium Water Content(%) | Equilibrium PEG/Water Content(%) |
|---|---|---|---|---|
| PUU I | — | 13.0 | 11.50 | 11.50 |
| PUU II | 10.01 | 32.0 | 24.24 | 31.82 |
| PUU III | 19.85 | 80.0 | 44.44 | 55.47 |
| PUU IV | 27.19 | 83.0 | 45.36 | 60.21 |
| PUU V | 35.60 | 99.0 | 49.75 | 67.64 |
| PUU VI | 43.18 | 140.0 | 58.33 | 76.32 |
| PUU VII | 48.34 | 167.0 | 62.54 | 80.65 |
| PUU VIII | 54.92 | 188.0 | 65.28 | 84.34 |
| PUU IX | 63.55 | 211.0 | 67.85 | 88.28 |
| PUU X | 68.98 | 275.0 | 73.33 | 91.73 |
| PUU XI | 75.41 | 517.0 | 83.79 | 96.01 |
| PUU XII | 83.18 | 784.0 | 88.69 | 98.10 |
| PUU XIII | 92.72 | 2680.0 | 96.40 | 99.74 |

Example 4

Introduction: The Stress-strain Behaviour of Polymeric Materials

A generalised stress-strain isotherm shown in FIG. 1 serves to define the useful mechanical properties that can be obtained from a stress-strain experiment.

Initial or Young's modulus, E. The initial slope of the curve, ('ab') determines the initial or Young's modulus, E. of the material. The sample is undergoing elastic deformation according to Hooke's Law, where the stress is directly proportional to the strain.

$$E = \frac{d\sigma}{d\varepsilon} \text{ as } \varepsilon \to 0$$

If the applied force is removed during this period, the sample will return to its original dimensions.

Yield Point/Stress. The Yield Point, 'c', is defined as the point at which elastic deformation ceases and plastic flow takes over. This is known as the elastic limit of the material. Not all materials have an observable yield point.

Stress at Failure. The point at which material fails under stress is shown by point 'd'. This ultimate stress is often quoted as the Tensile Strength of the sample.

Elongation at Failure. The maximum extension of a material at failure is given by point 'e'. This is normally presented as the Ultimate Strain.

$$\varepsilon_{max} = \frac{l_{(max} - l_O}{l_O}$$

where $\varepsilon_{max}$=The Ultimate Strain
$l_{max}$=Sample Length at Failure
$l_o$=Original Sample Length Energy to Break. The overall Toughness of a material is given by the amount of energy required to cause failure. Since energy is the product of the average applied force and distance, the energy to break or the toughness can be obtained from the area under the generalised stress-strain curve, ABCDE.

These characteristics of polymers are well known to those skilled in the art but are defined here to demonstrate the value of the presently claimed copolymers.

Stress-Strain Experiments

Stress-strain isotherms were determined for the series of linear block copolymer polyurethaneureas, prepared in Example 1 in the unswollen and equilibrium water-swollen states at 20° C. The experiments were performed on an Instron testing machine (model TH-M).

The Instron consists of two arms fitted with pneumatic sample clamps. The upper arm is fixed but the lower arm or crosshead can be raised or lowered by a gearing mechanism. The static arm is attached to a sensitive load cell. When the sample is stretched at a constant rate, the load applied to the sample is measured by the load cell and recorded on a chart recorder as a function of chart displacement. The experiments were carried out in a controlled environment with a constant temperature of 20° C. (293 K) and 65% relative humidity.

Sample Preparation

Solvent-cast films of the polyurethaneureas, PUU I to XIII, were prepared on glass plates from 5% w/v solutions of the polymers in chloroform. The films were equilibrated in double distilled water at 20° C. for 3 days. For the unswollen PUU stress-strain experiments, film samples were removed from the water and dried down in air for 24 hours and then in a vacuum oven for a further 24 hours to ensure the complete removal of water.

Standard "dumb-bell" shaped samples were cut from the films with a die.

The thicknesses of the samples were measured carefully using a micrometer, with the samples being placed between two glass microscope slides to minimise error through sample compression. The water-swollen test specimens were cut from the water-swollen films and re-immersed in the double distilled water. The two sets of samples were placed in the controlled environment of 20° C. and 65% relative humidity to equilibrate for 24 hours.

The Mechanical Properties of the Series of Linear Block Copolymer Polyurethaneureas at 20° C. and 65% Relative Humidity The mechanical properties obtained for the series of dry PUUs from their stress-strain isotherms are summarised in Table 5.

TABLE 5

| Polymer Reference | Weight Percent PEO5830 | Young's Modulus MNm$^{-2}$ | Yield Stress MNm$^{-2}$ | Ultimate Stress MNm$^{-2}$ | Ultimate Strain | Energy To Break MNm$^{-2}$ |
|---|---|---|---|---|---|---|
| PUU I | — | 2.395 | 0.823 | 17.168 | 11.667 | 48.096 |
| PUU II | 10.01 | 1.302 | 0.866 | 10.676 | 15.867 | 48.719 |
| PUU III | 19.85 | 1.923 | 1.096 | 3.823 | 19.283 | 38.245 |
| PUU IV | 27.19 | 3.720 | 1.686 | 8.890 | 13.900 | 57.626 |
| PUU V | 35.60 | 29.167 | 3.760 | 30.902 | 14.933 | 164.580 |
| PUU VI | 43.18 | 32.050 | 5.421 | 24.009 | 14.400 | 166.591 |
| PUU VII | 48.34 | 39.062 | 5.338 | 24.266 | 15.600 | 172.934 |
| PU VIII | 54.92 | 46.043 | 6.492 | 33.542 | 18.300 | 270.622 |
| PUU IX | 63.55 | 52.632 | 6.583 | 38.078 | 18.767 | 299.697 |
| PUU X | 68.98 | 57.870 | 7.664 | 41.386 | 17.150 | 303.611 |
| PUU XI | 75.41 | 86.806 | 8.890 | 24.218 | 11.917 | 156.298 |
| PUU XII | 83.18 | 94.697 | 9.036 | 23.750 | 10.483 | 129.490 |
| PUU XIII | 92.72 | 104.167 | 9.197 | 30.218 | 13.383 | 218.923 |

The Equilibrium Water-swollen Polyurethaneurea Films

The mechanical properties obtained for the series of water-swollen PUUs from their stress-strain isotherms are summarised in Table 6.

TABLE 6

| Polymer Reference | Weight Percent PEO5830 | Water Content (%) | Young's Modulus MNm$^{-2}$ | Ultimate Stress MNm$^{-2}$ | Ultimate Strain | Energy To Break MNm$^{-2}$ |
|---|---|---|---|---|---|---|
| PUU I | — | 3.85 | 0.866 | 1.616 | 10.767 | 9.043 |
| PUU II | 10.01 | 17.36 | 0.764 | 1.394 | 11.433 | 8.529 |
| PUU III | 19.85 | 36.71 | 0.780 | 10.343 | 14.400 | 46.003 |
| PUU IV | 27.19 | 45.05 | 0.830 | 13.795 | 14.333 | 67.313 |
| PUU V | 35.60 | 56.14 | 0.894 | 17.922 | 14.833 | 74.407 |
| PUU VI | 43.18 | 62.26 | 0.997 | 13.244 | 19.333 | 116.672 |
| PUU VII | 48.34 | 64.66 | 1.500 | 10.680 | 17.733 | 76.203 |
| PU VIII | 54.92 | 68.55 | 0.915 | 9.992 | 19.333 | 62.670 |
| PUU IX | 63.55 | 74.87 | 0.507 | 8.203 | 17.677 | 52.047 |
| PUU X | 68.98 | 79.51 | 0.368 | 4.088 | 14.100 | 21.372 |
| PUU XI | 75.41 | 85.25 | 0.147 | 0.417 | 13.967 | 4.093 |
| PUU XII | 83.18 | 89.70 | 0.054 | 0.478 | 13.667 | 3.511 |
| PUU XIII | 92.72 | 96.55 | 0.013 | 0.117 | 7.800 | 0.339 |

To demonstrate the benefit of the claimed copolymers Table 7 shows the Energy to Break (MNm$^{-2}$) for the PUU copolymers in the dry and swollen states, and the normalised energy to break for the swollen polymers as calculated by the equation $$\text{Normalised Energy to Break} = \frac{\text{Energy to Break (Swollen Polymer)}}{\text{Wt. Fraction Polymer in Swollen Sample}}$$

TABLE 7

| Polymer Reference | Swollen Polymer Content (Wt. Fraction) | Energy to Break (MNm$^{-2}$) Dry | Swollen | Normalised | Retained strength in swollen state as percentage of strength in dry state |
|---|---|---|---|---|---|
| PUU I | 0.961 | 48.096 | 9.043 | 9.410 | 18.80 |
| PUU II | 0.826 | 48.719 | 8.529 | 10.326 | 17.51 |
| PUU III | 0.633 | 38.245 | 46.003 | 72.674 | 120.29 |
| PUU IV | 0.550 | 57.626 | 67.313 | 122.933 | 116.81 |
| PUU V | 0.439 | 164.580 | 74.407 | 169.492 | 45.21 |
| PUU VI | 0.377 | 166.591 | 116.672 | 309.475 | 70.03 |
| PUU VII | 0.353 | 172.934 | 76.203 | 215.872 | 44.01 |
| PU VIII | 0.314 | 270.622 | 62.670 | 199.586 | 23.16 |
| PUU IX | 0.251 | 299.697 | 52.047 | 207.358 | 17.37 |
| PUU X | 0.205 | 303.611 | 21.372 | 104.254 | 7.04 |
| PUU XI | 0.148 | 156.298 | 4.093 | 27.655 | 2.67 |
| PUU XII | 0.103 | 129.490 | 3.511 | 34.087 | 2.71 |
| PUU XIII | 0.034 | 218.923 | 0.339 | 9.970 | 0.15 |

From Table 7 it is easy to see the benefit of the claimed copolymers. The copolymers PUU II to PUU XII all retain to a degree their mechanical strength in the swollen state. The preferred PUU copolymers are those whose energy to break in the swollen state is at least 15% of that in the dry state.

Figure 2:
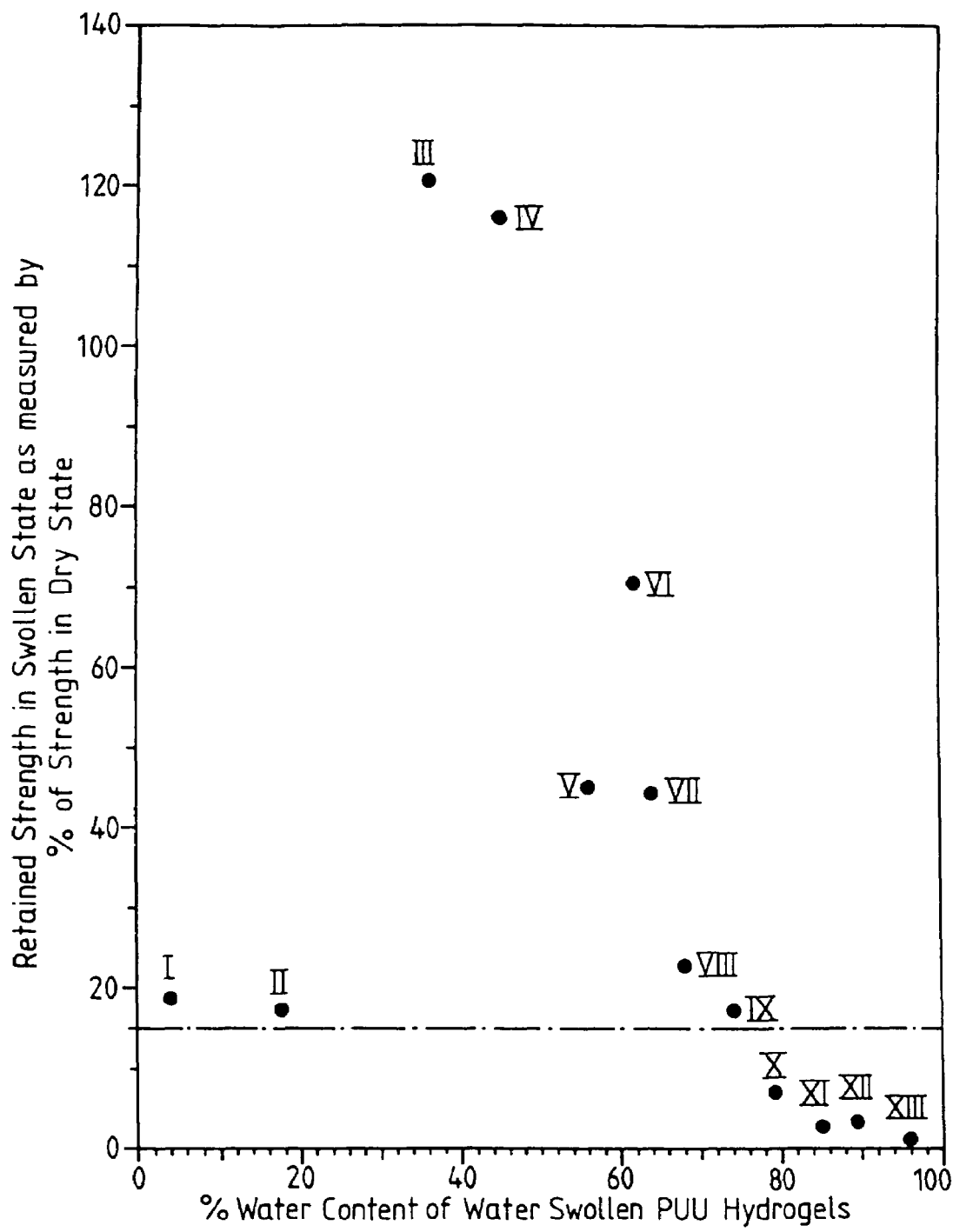
FIG. 2 is a plot of Energy to Break ($MNm^{-2}$) plotted against Equilibrium Water Content of the series I to XIII.

This is further shown in FIG. 2, where the Energy to Break (MNm$^{-2}$) is plotted against the Equilibrium Water Content of the series I to XIII.

Figure 3:
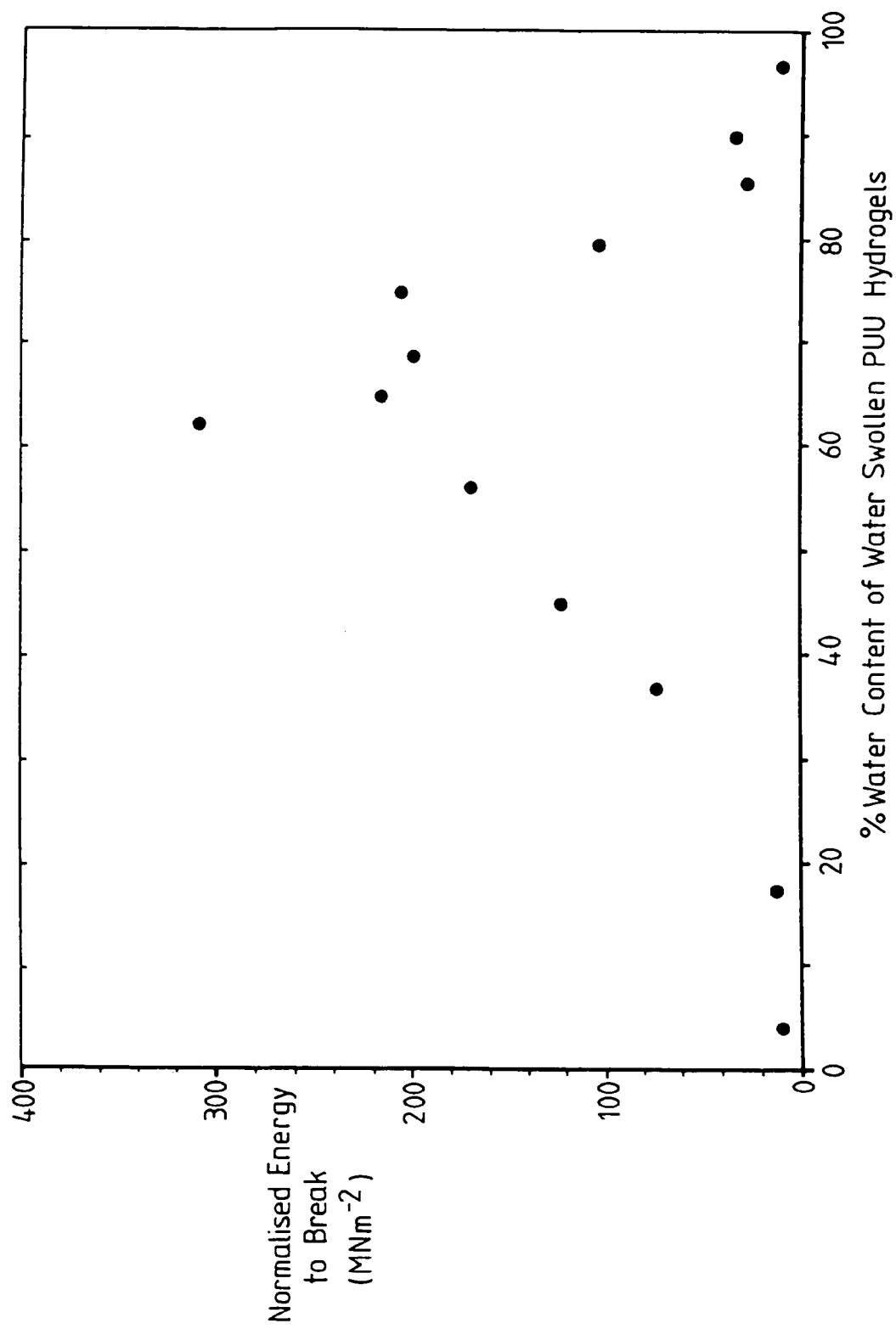
FIG. 3 is a Normalized Energy to Break ($Nm^{-2}$) of the swollen polymers.

FIG. 3 shows the Normalised Energy to Break (Nm$^{-2}$) of the swollen polymers wherein it can be seen that the copolymers PUU II to XII are advantageous over the solvent soluble chain extended polymers PUU I and PUU XIII.

Example 5

Complexed Polyurethaneurea Copolymer (PUU) Poly(acrylic acid) (PAA) Membranes

A wide range of compositions of PUU/PAA membranes have been prepared in an unsupported form suitable for the laboratory determination of permeability and selectivity to neutral and charged solutes over a range of molecular weights (M.W.~100-~10,000). The unsupported PUU/PAA complexed membranes can be prepared by casting the solutions onto glass plates or by using multiple casts on a film spinner. Twenty applications of 5% w/v solutions of the copolymer complexes in methanol/acetic acid produce membranes with thicknesses of approximately 115 μm.

The initial PUU/PAA membrane formulations were based on PUU VI (43.18% PEO5830) and contained up to 50% by weight of poly(acrylic acid). These membrane formulations exhibited large extremes in swelling (500 pph-50 pph) in response to changes in pH. However, their mechanical strength particularly at high pH was poor. This problem was overcome by using PUU formulations with lower PEO contents (<20%) and blending these lower swelling polymers with smaller amounts of the poly(acid), (typically, less than 30% PAA by weight). The resulting strong, homogeneous membranes exhibit a reversible pH 2.2-pH 8.0 response with swelling extremes ranging from ~10 pph to ~300 pph. The swelling response of these membranes to changes in pH has also led to their investigation as a potential component in the development of a novel pH responsive value.

Preparation of the Poly(acid)-complexed Membrane Formulation, PUU II 10% PAA

The novel linear polyurethaneurea hydrogel composition, PUU II, containing ~10% by weight of PEO5830 was used in the preparation of the PUU II/10% PAA membranes.

| Polymer Reference: | PUU II |
|---|---|
| PEO5830 Content: | 10.01% |
| Water Uptake: | ~21 pph (17%) at 21° C. |
| | ~32 pph (24%) at 37° C. |

The poly(acid) complexed membrane was prepared from poly(acrylic acid), MW 450,000, and the polyurethaneurea formulation, PUU II. The PUU II composition was blended in solution with 10% by weight of PAA using a solvent composition of 9 parts methanol to 1 part glacial acetic acid. Ethanol and propanol may also be used in the solvent formulation (i.e. 9 parts alcohol to 1 part glacial acetic acid). Typical solution concentrations would be 5-10% w/v polymer in solvent.

Polyacid complexed PUU membranes can be prepared by casting the PUU/PAA solutions onto glass plates or petri dishes and allowing the solvent to evaporate over 24 hours. High quality, reproducible membrane films can be prepared using a spin-casting technique. After casting, the PUU/PAA membranes should be washed in distilled water to remove any residual solvent. A variety of membrane type devices or coatings can be prepared from the polyacid-complexed PUU solutions.

The polyacid-complexed formulations PUU VI/10-70% PAA, PUU III/10% PAA and PUU III/20% PAA have also been prepared.

Poly(acrylic acid) with a molecular weight of 450,000 has been used in all the acid-complexed membrane formulations prepared so far. PAA is commercially available in molecular weights ranging from a few hundred to several million. Useful PUU/PAA formulations should use a PAA with a molecular weight of at least 1000. Preferred formulations should also have a ratio of PAA acid groups to PEO ether groups of 1:1 or less (e.g. 0.1:1). In some cases it may be desirable to increase the ratio of acid groups to PEO ether groups (e.g. 3:1). The PAA limit should be set at 70% by weight of the complex, as above this amount of acid it is difficult to produce a homogeneous product.

Swelling experiments were carried out on the complexed film samples in a range of citrate-phosphate buffer solutions at 21° C. and 37° C.

The results are shown below. Table 8 shows the variation in rate of swelling of the complex membrane PUU II/10% PAA.

TABLE 8

| | SWELLING, pph | |
|---|---|---|
| pH | 21° C. | 37° C. |
| 2.2 | 15.1 | 11.1 |
| 2.6 | 12.3 | 14.9 |
| 3.0 | 11.8 | 11.0 |
| 3.6 | 12.6 | 13.3 |
| 4.0 | 20.7 | 19.0 |
| 4.4 | 94.0 | 95.0 |
| 5.0 | 158.2 | 150.7 |
| 6.0 | 166.7 | 151.1 |
| 7.0 | 122.0 | 126.5 |
| 8.0 | 113.4 | 119.3 |

Table 9 shows the variation in the equilibrium swelling of the complex membrane PUU III/20% PAA.

TABLE 9

| pH | SWELLING, pph 37° C. |
|---|---|
| 2.2 | 25.6 |
| 2.6 | 27.1 |
| 3.0 | 27.4 |
| 3.6 | 32.8 |
| 4.0 | 58.0 |
| 4.4 | 196.3 |
| 5.0 | 293.3 |
| 6.0 | 407.4 |
| 7.0 | 282.7 |
| 8.0 | 246.0 |

Example 6

PUU prepared using 0.2% by weight of diamine

| | PEG5830 | PPG425 | DADP | DW |
|---|---|---|---|---|
| No. of moles | 1.0 | 72.0 | 0.573 | 77.252 |
| Weight Percent | 10.26 | 53.85 | 0.20 | 35.69 |

Example 7

PUU prepared using 2.0% by weight of diamine

| | PEG5830 | PPG425 | DADP | DW |
|---|---|---|---|---|
| No. of moles | 1.0 | 10.0 | 1.369 | 13.008 |
| Weight Percent | 42.34 | 30.86 | 2.00 | 24.80 |

Examples 8-10

PUU Hydrogels Prepared Using an Aliphatic Diamine

Examples of the linear block copolymer PUU hydrogels were prepared using an aliphatic diamine. The aliphatic diamine used was hexanediamine. Aliphatic diamines are incompatible with the ferric chloride catalyst and so stannous octoate was used as an alternative catalyst. The concentration of the stannous octoate catalyst was 0.1% by weight of the total reactants. The polymerisation procedure was the same as previously described although care was taken in the addition of the aliphatic diamine due to the hygroscopicity of aliphatic diamines.

Example 8

| | PEG5860 | PPG425 | HD | DW |
|---|---|---|---|---|
| No. of moles | 1.0 | 72.0 | 0.980 | 77.679 |
| Weight Percent | 10.29 | 53.72 | 0.20 | 35.79 |

The resulting polymer was dissolved in methanol and a hydrogel film cast in a petri dish through solvent evaporation. A sample of the hydrogel film was placed in double distilled water and its water uptake at 21° C. was measured. The hydrogel film was strong and tough in the dry and swollen states.

| Equilibrium Water Uptake, 21° C. | ~30 parts per hundred (pph) |
|---|---|
| Equilibrium Water Content, 21° C. | ~23% by weight |

Example 9

|  | PEG5860 | PPG425 | HD | DW |
|---|---|---|---|---|
| No. of moles | 1.0 | 10.0 | 0.500 | 12.075 |
| Weight Percent | 43.94 | 31.86 | 0.436 | 23.76 |

The resulting polymer was dissolved in methanol and a hydrogel film cast in a petri dish through solvent evaporation. A sample of the hydrogel film was placed in double distilled water and its water uptake at 21° C. was measured. The hydrogel film was strong and tough in the dry and swollen states.

| Equilibrium Water Uptake, 21° C. | ~175 parts per hundred (pph) |
|---|---|
| Equilibrium Water Content, 21° C. | ~64% by weight |

Example 10

|  | PEG5860 | PPG425 | HD | DW |
|---|---|---|---|---|
| No. of moles | 1.0 | 10.0 | 0.250 | 11.812 |
| Weight Percent | 44.26 | 32.10 | 0.219 | 23.42 |

The resulting polymer was dissolved in methanol and a hydrogel film cast in a petri dish through solvent evaporation. A sample of the hydrogel film was placed in double distilled water and its water uptake at 21° C. was measured. The hydrogel film was strong and tough in the dry and swollen states.

| Equilibrium Water Uptake, 21° C. | ~180 parts per hundred (pph) |
|---|---|
| Equilibrium Water Content, 21° C. | ~64% by weight |

Example 11

A variety of linear block copolymer polyurethaneureas can be prepared using polymeric segments other than poly(propylene oxide). These segments, through their hydrophobicity, can be used to control the hydrophilicity and therefore the aqueous swellability of the PUU composition. These alternative polymeric segments can also improve the mechanical strength of the PUU hydrogels.

Some examples of alternative blocks which may be used in conjunction with poly(ethylene glycol) to produce strong, linear PUU hydrogels are polyols derived from poly(tetramethylene oxide), poly(isobutylene), poly(ethylene adipate), poly(tetramethylene adipate), poly(caprolactone), poly(butadiene) and hydroxybutyl terminated poly(dimethylsiloxane). A constraint on the "one shot" melt polymerisation process is that all of the reactants from a homogeneous mixture in the molten state.

A linear polyurethaneurea hydrogel was prepared using poly(tetramethylene glycol) with a molecular weight of 650 (i.e. PTMG650) as an alternative segment to the PPG425. The experimental procedure was the same as for the PEG/PPG based PUUs. PUU prepared using PTMG650.

|  | PEG5860 | PTMG650 | DADP | DW |
|---|---|---|---|---|
| No of moles | 1.0 | 8.0 | 0.851 | 10.344 |
| Weight Percent | 42.02 | 37.29 | 1.21 | 19.47 |

The resulting polymer was dissolved in methanol and a hydrogel film cast in a petri-dish through solvent evaporation. A sample of the hydrogel film was placed in double distilled water and its water uptake at 21° C. was measured. The hydrogel film was strong and tough in the dry and swollen states.

The invention claimed is:

1. An organic solvent-soluble linear random block copolymer hydrogel containing discrete polymeric first and second segments, the first segments comprising hydrophilic mainly polyethylene oxide segments —(CH$_2$CH$_2$O)$_n$—, the second segments being of relatively more hydrophobic character than the first segments, wherein the second polymer segments are disposed randomly in the polymer chain as discrete blocks, successive segments being connected through urethane —NHCOO— linkages to hydrophobic connecting segments, a minor proportion of which also containing urea —NHCONH— groups, which urea groups are present as units of formula

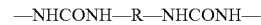

—NHCONH—R—NHCONH— wherein R represents a hydrocarbyl group, all of said first, second, and connecting segments being randomly distributed throughout the copolymer, the proportion of urea groups comprising from 0.1 to 5.0% by weight of the copolymer.

2. A copolymer hydrogel according to claim 1, in which the hydrophilic segments comprise mainly polyethylene oxide (PEO) residues and a minor amount of an additional component derived from other alkylene oxides, epihalohydrins, cyclic mono or poly ethers including oxetane, tetrahydrofuran, dihydrofuran, dihydropyran, dioxolane and trioxane and N[epoxy substituted] heterocyclic compounds such as N-[2,3-epoxy-propyl]-pyrolidone.

3. A copolymer hydrogel according to claim 2, in which the hydrophilic segment contains up to 25% by weight of groups derived from propylene oxide, 1,2, epoxybutane or 2,3, epoxybutane.

4. A copolymer hydrogel according to claim 1 in which the second segments are derived from a polymer which, together with the polyethylene oxide (PEO), will form a homogeneous melt or solvent solution of the component polymers from which the copolymer product can be formed by a polymerisation reaction.

5. A copolymer hydrogel according to claim 1, in which the second segments comprise polypropylene oxide (PPO) segments —(CH(CH$_3$)CH$_2$O—)$_n$—.

6. A copolymer hydrogel according to claim 1 in which the relative proportions of the hydrophilic PEO segments and the second segments, are from 5 to 90% PEO and 55 to 5% of the second segments.

7. A copolymer hydrogel according to claim 1 in which the relative proportions of the hydrophilic PEO segments and the second segments are from 30 to 60% PEO and from 45 to 15% of the second segments.

8. A copolymer hydrogel according to claim 1, wherein the polyethylene oxide segments are comprised of homopolymeric polyethylene oxide having a number average molecular weight of from 1,000 to 20,000.

9. A copolymer hydrogel according to claim 5, wherein the polypropylene oxide segments are comprised of homopolymeric polypropylene oxide having a number average molecular weight of from 250 to 6,000.

10. A copolymer hydrogel according to claim 1, in which the more hydrophobic second segments are derived from a hydroxy or amine terminated polyol derived from polytetramethylene oxide, polyisobutylene, polyethylene adipate, polytetramethylene adipate, polycaprolactone, polybutadiene and hydroxybutyl terminated polydimethylsiloxane.

11. A copolymer hydrogel according to claim 1, wherein the toughness of the copolymers in the dry state as calculated by measuring the area under the curve of the stress-strain isotherm is retained to at least 15% when the copolymers are swollen.

12. A copolymer hydrogel according to claim 11, wherein the energy to break of the swollen copolymer is at least 40% of that of the copolymer in the dry state.

13. A copolymer hydrogel according to claim 1 4comprising units of the formula

X—OOCNH—R—NHCONH—R'—NHCONH—R—NHCOO—Y wherein X represents a polyethylene oxide segment, Y represents a second segment and R and R' which may be the same or different represent hydrocarbyl groups comprising from 2 to 20 carbon atoms.

14. A copolymer hydrogel according to claim 13, also comprising a smaller proportion of units of the formula X—NHCONH—(R")$_a$—NHCONH—Y wherein X represents a hydrophilic polyethylene oxide segment, Y represents a second segment, a is 0 or 1 and R" represents a hydrocarbyl group comprising from 2 to 20 carbon atoms.

15. A copolymer hydrogel according to claim 13, wherein R and R" represent an aliphatic group and R' represents an aromatic group.

16. A copolymer hydrogel according to claim 15, wherein R' is 1,2-cyclohexylene or a 4,4'-diphenylmethane group.

17. A copolymer hydrogel according to claim 15 wherein R and R" are hexamethylene, isophorone or 4,4'-dicyclohexylmethane groups.

18. A copolymer hydrogel according to claim 14, wherein R" represents a group having the formula

[R—X—R]-n or [R—Y—R]-m wherein R represents a hydrocarbyl group having from 2 to 20 carbon atoms, X represents a polyethylene oxide group, Y represents a polypropylene oxide group and n and m being an integer having a value of at least 1, n and m being the same or different.

19. A copolymer hydrogel according to claim 18, wherein R represents a hexamethylene, isophorone or 4,4'-dicyclohexylmethane group.

20. Shaped articles prepared from a copolymer according to claim 1.

21. Articles coated with a copolymer according to claim 1.

* * * * *